United States Patent [19]

Opie et al.

[11] Patent Number: 4,679,557

[45] Date of Patent: Jul. 14, 1987

[54] ELECTRODYNAMIC TRANSLUMINAL ANGIOPLASTY SYSTEM

[75] Inventors: Eric A. Opie; Thomas J. Clement, both of Seattle, Wash.

[73] Assignee: E. R. Squibb & Sons, Inc., Princeton, N.J.

[21] Appl. No.: 649,101

[22] Filed: Sep. 10, 1984

[51] Int. Cl.⁴ ............................................. A61B 17/32
[52] U.S. Cl. .................................... 128/305; 128/752
[58] Field of Search ............... 128/305, 749, 751, 752, 128/753, 754, 303 R; 604/22, 35

[56] References Cited

U.S. PATENT DOCUMENTS

4,445,509  5/1984  Auth ..................................... 128/305

Primary Examiner—Gene Mancene
Assistant Examiner—David I. Tarnoff
Attorney, Agent, or Firm—Lawrence S. Levinson; Sanford J. Asman

[57] ABSTRACT

An electromechanical system which may be used in conjunction with spinning catheters, such as those which have differential cutting burrs, includes an electric prime mover which attaches to an advancer assembly. The advancer assembly has an off-axis drive and apparatus for loading a catheter unit, which is driven through a catheter engagement coupling. The catheter assembly can also include one or two lumens with access ports at the advancer assembly, whereby medicines may be injected or pressure readings may be obtained from the vessel.

14 Claims, 11 Drawing Figures

TORQUE CONTROL WITH DYNAMIC BRAKE

ELECTRODYNAMIC TRANSLUMINAL ANGIOPLASTY SYSTEM

BACKGROUND OF THE INVENTION

The present invention relates to a device for driving surgical instruments. In particular, it relates to a device of the type which can be used for driving rotating transluminal catheters, such as those which are capable of differential cutting.

Impairment of blood circulation caused by deposits of atherosclerotic plaque on the inner walls of arteries is a major cause of artery disease. Vaso-restrictions resulting in loss of adequate circulation can lead to coronary infarction (heart attack), impairment of peripheral organ function, loss of limbs, and other ills. Procedures, such as surgical bypass, endarterectomy, and balloon angioplasty, have been used in recent times to regain patency. Both bypass and endarterectomy are invasive techniques that are not always successful. Balloon angioplasty has been used with success, but patient selection criteria are restrictive. Also, balloon angioplasty, while the least invasive method, does not remove the obstruction. It simply pushes it aside.

Due to each method's respective deficiencies, a less invasive technique to remove plaque deposits is needed. One such method is described in U.S. Pat. No. 4,445,509 entitled METHOD AND APPARATUS FOR REMOVAL OF ENCLOSED ABNORMAL DEPOSITS which issued on May 1, 1984 to David C. Auth. The method involves the removal of plaque by cutting it away from the arterial wall using a differential cutting apparatus. This method allows for the removal of plaque without significant damage to the endothelial lining of a vessel and is applicable to catheter techniques.

Differential cutting is a process in which a difference in hardness of materials is exploited. If a relatively hard material exists over a softer substrate, then it is possible to cut the harder material away with a fluted edge cutter of appropriate velocity and frequency without cutting the substrate. The cutting edge pushes the softer material aside, but the harder material, not being as pliable, is cut before it can move away.

A spinning burr of appropriate design is advanced to the lesion by conventional percutaneous cut-down procedures. Vascular access via well known catheter techniques are used to advance a guide wire of appropriate design through the lesion. Then, a drive catheter with a differential cutting head is advanced to the lesion within a guide sheath. The guide sheath is used to protect the endothelial lining from unnecessary abuse and to stabilize the drive catheter.

SUMMARY OF THE INVENTION

The support equipment used to service the differential cutting catheters is the subject of this invention. Such equipment must be capable of operating over a guide wire in order to direct the drive catheter through the tortuous path needed to approach a lesion within a vessel. A hydraulic channel must exist between the cutting head and the proximal end of the catheter. The channel must be accessible while the catheter is spinning at high speed, and it must support both vacuum and high pressures. The channel may be used for debris removal, injections of chemical agents, and distal pressure measurement. There must be a guide sheath to support the drive catheter to prevent looping and to protect the arterial walls from abrasion. The guide sheath is also used to deliver fluids, such as medications, and to make pressure measurements proximal to lesions. To perform this task, the sheath must have a lumen access point, and, on demand, it must be able to form a seal between itself and the catheter at its proximal end.

A method must exist to smoothly and accurately advance the drive catheter with respect to the guide sheath in order to allow the operator to advance the differential cutting head into the lesion to cut it away.

The instrument must be safe to use. With a high speed spinning member within the arterial system, the potential for injury to the patient in the event of catheter breakage or augering of the burr is significant. A method should exist to test the condition of the operating system, and, if a problem were to arise, the drive shaft should be stopped as rapidly as possible to prevent undue torsional stressing of vessels.

The system must accommodate different sized burrs and allow for their replacement in an efficient and simple manner, thereby allowing the operator to cascade sizes.

The system of the present invention is able to rotate the differential cutting head at a rotational velocity of at least 15,000 rpm with a delivered torque of approximately 2 inch-ounces. Also, it is hemo-compatible, i.e., all materials that come in contact with the circulatory system are physiologically compatible and sterilizable.

DETAILED DESCRIPTION OF THE PREFERRED EMBODIMENT

Figures 1, 3:
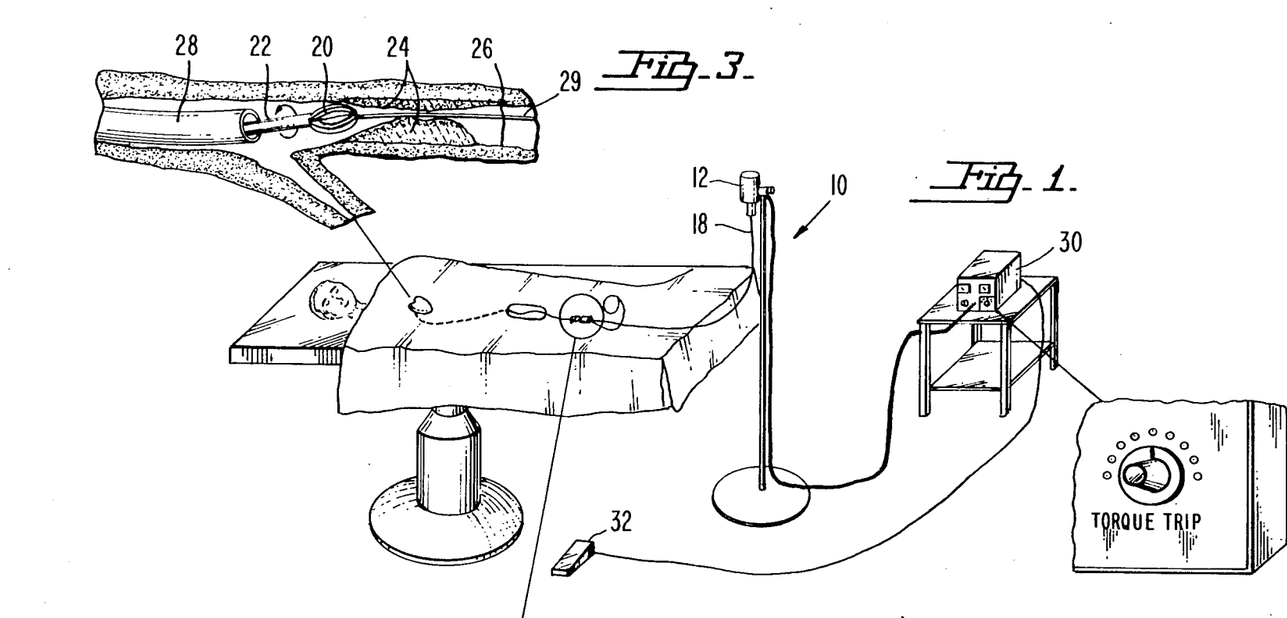
FIG. 1 is a pictorial view showing the present invention in use.
FIG. 3 is a cross-sectional view showing the cutting head of the pesent invention in use removing a lesion from within a vessel.
Figure 2:
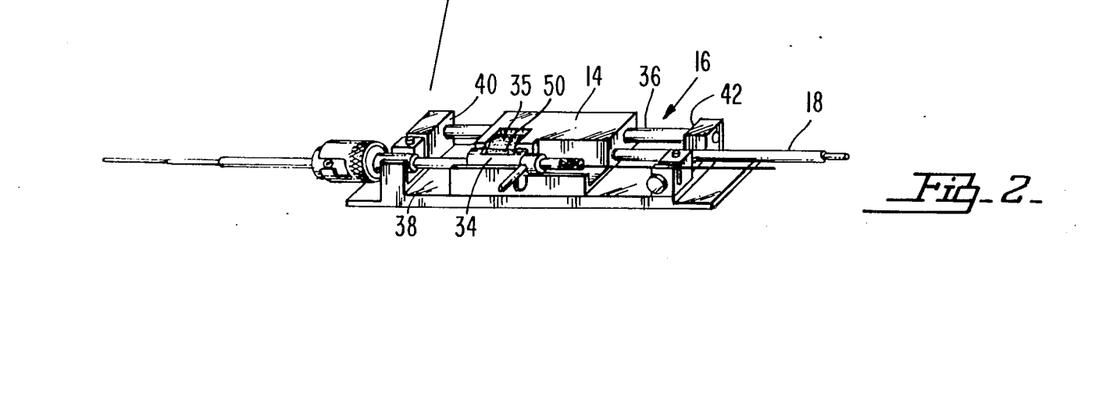
FIG. 2 is a pictorial view of the advancer assembly of the present invention.

It is the primary object of this invention to provide for the previously mentioned requirements, and to do so in a manner that is convenient for the operator. Referring generally to FIGS. 1-3, the system 10, of the present invention, meets the needed requirements. The system 10 uses an electric prime mover 12 whose output is connected to the carriage 14 of an advancer assembly 16 via a flexible drive shaft 18. The motor 12 is capable of developing 20,000 rpm with the torque needed at that speed to overcome frictional losses and to drive a cutting head 20 which is attached to a drive catheter 22, as shown in FIG. 3. The cutting head 20, which extends out of a tubular guide sheath 28, and which is guided by a guide wire 29, is used to cut a lesion 24 within a vessel 26.

Powering the motor 12 is a load sensing power supply 30 which will stop the motor 12 and assembly 16 with dynamic braking if the drive catheter 22 or cutting head 20 binds. This combination improves the safety of the system 10 by preventing undue stress on the vessel 26. It will rapidly stop the differential cutting head 20 in the event of a failure, such as augering, catheter breakage, or jamming by debris. These safety precautions should prevent the vessel 26 from being torqued excessively, thus preventing torn connective tissues, perforated vessels, and damaged catheters.

To make the system 10 easier to use, the power supply 30 automatically corrects for accelerations and decelerations of the drive catheter 22 by continuously testing the load on the prime mover 12. This prevents the inertia of the system 10 from falsely tripping the torque limit of the power supply when the operator accelerates the drive shaft 18 and the other rotating components and prevents augmenting the differential torque threshold when the operator decelerates the rotating components.

Since the size and length of drive catheters 22 is variable, it is necessary to include a variable torque trip point in the design. This allows the operator to correct for catheter drag, aggravated by bends in the drive catheter 22 needed to access lesions, and for different burr diameters, i.e., cutting head 20 sizes. The variable torque trip point further permits the operator to correct for parasitic loads in order to maintain an appropriate safety margin in all possible positions and loads of the drive catheter 22 thereon.

Catheter drag can be measured easily by simply reducing the threshold of the torque trip control until the system 10 stops. This is done while the system 10 is running in place, with the differential cutting head 20 retracted into the guide sheath 28. The threshold can then be increased as needed to allow for normal cutting loads. The increment would be different for different sizes and types of burrs. To accommodate different diameter drive assemblies, the rotational velocity of the head must be adjustable. This is accomplished by controlling the power supply 30 using a foot pedal 32.

The advancer assembly 16, shown in FIGS. 2 and 4–6, allows the operator to move the differential cutting head 20 with respect to the guide sheath 28 smoothly and accurately. The advancer assembly 16 includes a carriage 14 which supports a catheter engagement coupling 34 and houses a driving wheel 35. To advance the drive catheter 22, the carriage 14 is simply moved by hand along a guide rail 36 to any position within the bounds of the saddle 38, i.e, movement of the carriage 14 along the guide rail 36 is permitted within the bounds of the front and rear walls 40, 42, respectively. The catheter engagement coupling 34 snaps into the carriage 14, simply by pressing it into its receptacle 44 (See FIG. 5), and it is removed in a similar manner. The guide sheath 28 slips into a universal alignment block 46 on the front of the saddle 38 and the guide wire 29 clamps into a similar block 48 in the rear of the saddle 38. These receptacles 46, 48 make catheter changes quick and easy.

The process of loading the catheter assembly uses a number of features of the advancer 16. The carriage 14 follows a single, round guide rail 36 which allows the carriage 14 to pivot to load the catheter engagement coupling 34. In order to do so, the carriage 14 is pivoted up, and the catheter engagement coupling 34 is snapped into place. The guide sheath 28 and guide wire 29 are then locked into position by lowering the carriage 14 to its running position while aligning the proximal end 45 of the sheath 28 with its slip fit receptacle 46. Once the proximal end 45 of the sheath 28 has engaged the receptacle 46, the carriage 14 is advanced along the guide rail 36 to its fully advanced position, i.e., toward the front wall 40. This seats the guide sheath 28 in its receptacle 46 and aligns the guide sheath 28 with the carriage 14 for minimum friction between the catheter 22 and the guide sheath 28. The alignment blocks 47, 48 are adjustable to accommodate any horizontal misalignment. The guide wire 29 similarly slips into its receptacle 51 at the rear wall 42 of the saddle 38 and is clamped in place using a screw clamp operated by a knob 49. The system 10 is then ready for use.

Rotational energy is coupled to the drive catheter 22 by the engagement of the drive wheel 35 in the carriage 14 with a driven wheel 50 within the catheter engagement coupling 34 (See FIGS. 2 and 4–6). The wheels 35, 50 are preferably made of aluminum and urethane foam, respectively. The urethane driven wheel 50 compresses in the interface between the wheels 35, 50 and thereby sets the preload between the wheels 35, 50. It also has a high coefficient of friction which reduces slippage. The off-axis drive facilitates the coaxial exit of the guide wire 29 and thereby eases the assembly and disassembly of the catheter elements. With this feature, catheter elements can be telescoped together independent of the drive assembly, and, when ready, the entire assembly can be snapped into the advancer 16.

Figure 6:
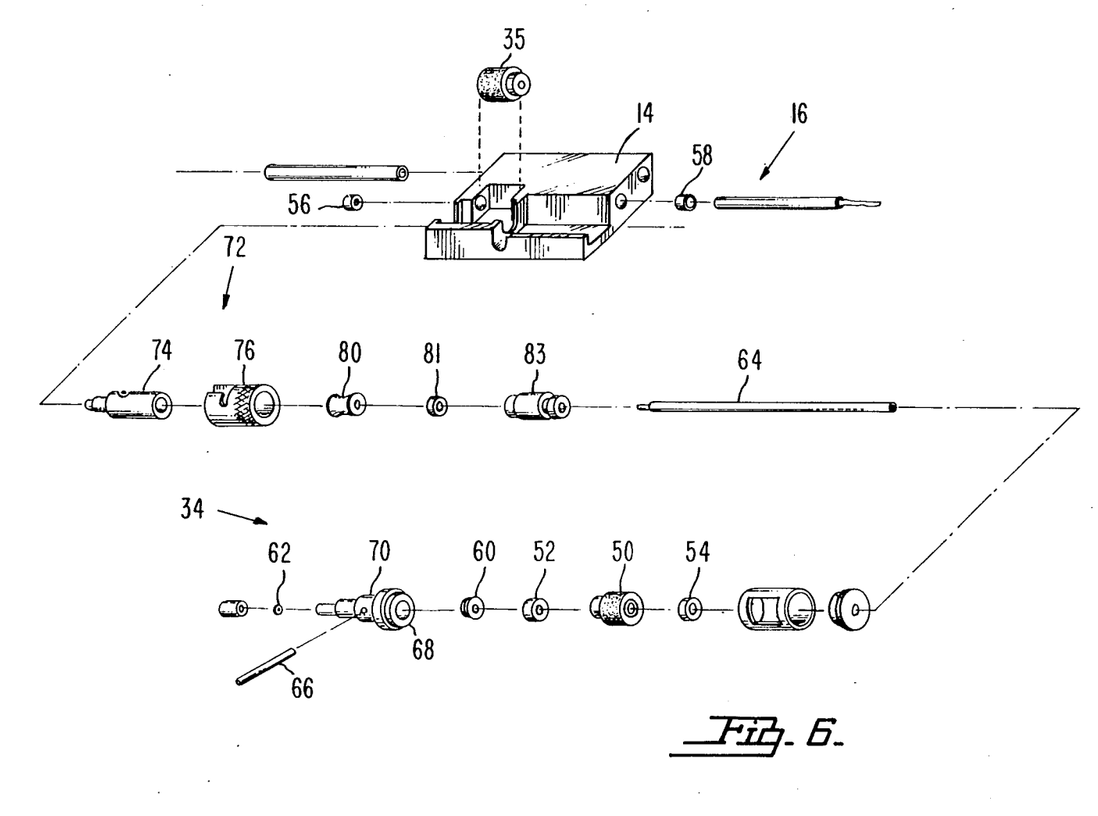
FIG. 6 is a pictorial view showing the parts of the advancer assembly.

Referring to FIG. 6, the catheter engagement coupling 34, which is an integral part of the catheter, houses the support bearings 52, 54, and seals 60, 62. To form a seal on the guide wire 29, a linear seal 62 is used. The linear seal 62 runs on a semi-rigid section 78 of the guide wire 29 (See FIG. 7A). The semi-rigid section 78 is preferably made of stainless steel tubing or wire. The seal 60 is a rotational seal which isolates the access tube 66 and cavity 68 within an end cap 70. The two seals 60, 62 work together to allow the lumen between the drive catheter 22 and the guide wire 29 to be accessed under operating conditions, thereby allowing the operator to withdraw or inject fluids at any time during the procedure. There is a rigid drive catheter shaft 64 which extends from the catheter engagement coupling 34 into the guide sheath 28 to prevent looping of the flexible drive portion of the catheter 22 when the carriage 14 is withdrawn from the fully advanced position. If the flexible shaft was withdrawn from the sheath and left unsupported between the lumen of the guide sheath and the catheter engagement coupling 34, it would tend to whip and loop. The rigid shaft 64 prevents the flexible portion of the drive catheter 22 from being exposed.

The guide wire 29 used in current vascular therapy is comprised of a spring coil wound with small diameter wires. The resulting coils are from about 0.016 inches to about 0.045 inches in diameter and can be up to 2 meters long. Recently, solid tube guide wire bodies have been introduced by various companies, but only in the smallest size (0.016 inches).

Figures 7A, 7C:
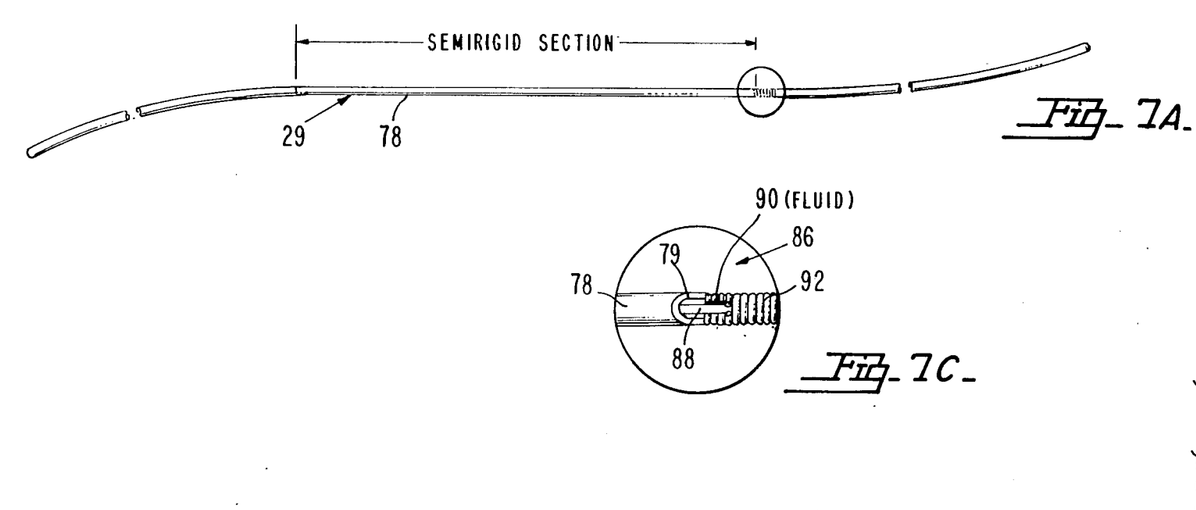
FIG. 7A is a side view of a section of the guide wire used with the present invention.
FIGS. 7B and 7C are exploded views illustrating alternative embodiments of a portion of FIG. 7A.
Figure 7B:
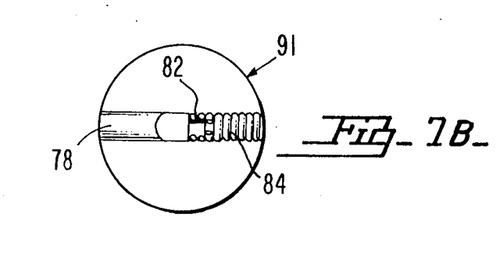

The solid tube type guide wires can be used directly with the present system 10, but the coiled variety cannot. Carriage movement requires that the guide wire move in and out of the catheter engagement coupling 34. To allow for this movement, while maintaining a sealed hydraulic channel, a linear seal must be maintained between the catheter engagement coupling 34 and the guide wire 29. The linear seal 62 within the catheter engagement coupling 34 performs this task. To seal on the guide wire 29, its exterior surface must be smooth and even within the area of movement of the seal 62. To provide for this, coiled guide wires must have integrated a small semi-rigid section 78, preferably of stainless steel tube or rod, of the same or larger diameter in the area of the advancer 16, as shown in FIGS. 7A–7C. Thus, the physical characteristics of the guide wire 29 are unchanged for the most part, but it will be sealable.

Both movable and fixed core guide wires, shown in FIGS. 7B and 7C, respectively, are possible with this type of guide wire 29. The fixed core type 91 is simpler, in that its core 82 and coil 84 are bonded to the end of the semi-rigid section 78. The movable core type 86 is more complex in that its core 88 must pass through a tubular semi-rigid section 78. The tube that comprises the semi-rigid section 78 must not allow fluids to escape from the catheter lumen formed between the core 88 and the tube 78, so a seal is needed between the core wire 88 and the tube lumen 78. This is accomplished by using a close tolerance seal between the tube 78 and the core wire 88. Some silicone oil 90 helps in maintaining the seal. The movable core version 86 would, of course, have the coil 92 bonded to the tubing section 78 of the guide wire 29.

With these types of guide wires, it is then possible to hold them fixed with respect to the advancer 16 and maintain a fluid tight seal. The semi-rigid section 78 can be made as long or positioned as required to advance the distal tip of the guide wire 29 out of the orifice of the differential cutting head 20 as far as needed. The only requirement is that the semi-rigid section 78 must ride within the lumen of the seal 62 inside the catheter engagement coupling 34 when operating the system 10.

Figure 4:
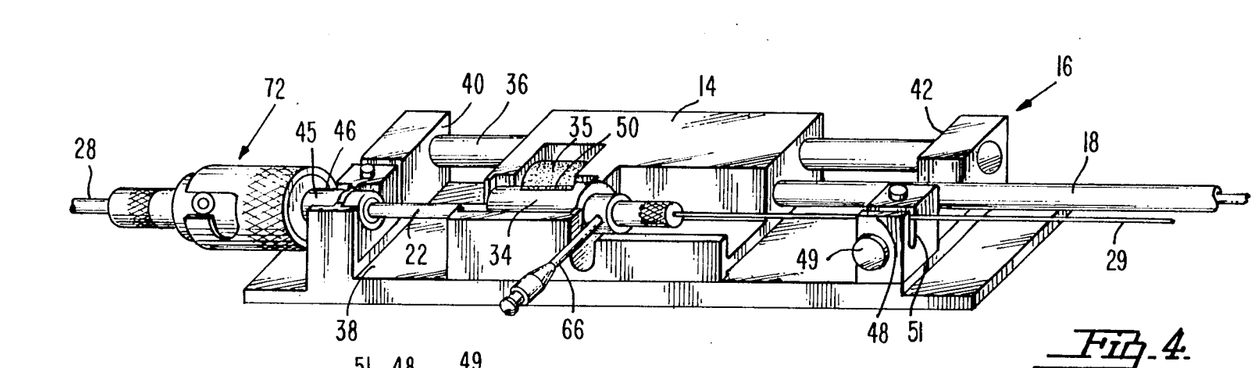
FIGS. 4 and 5 are pictorial views of the advancer assembly of the present invention.
Figure 5:
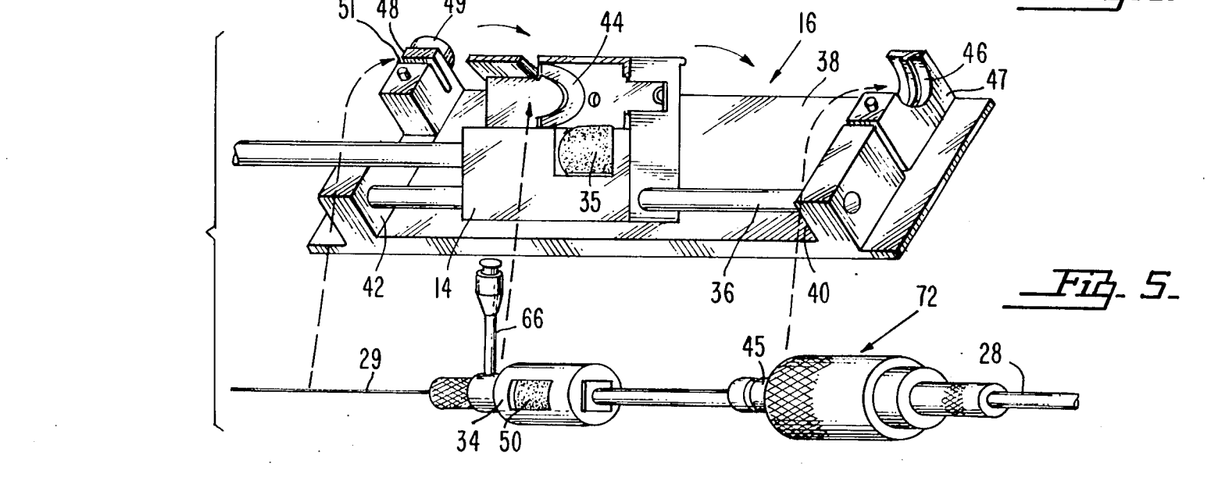

Referring generally to FIGS. 4–6, the lumen access valve 72 includes a body 74, an engagement sleeve 76, a thrust washer 81, and an end cap with a clamping fixture 83. It is attached to the distal end of the sheath 28 where it provides a method of sealing the distal end of the guide sheath 28 and a coupling point for fluid connections. The valve 72 uses an expanding gasket seal 80. When the valve 72 is open, the seal element 80 is removed from contact with the rigid portion 64 of the drive shaft 22 to protect the seal element 80 from the abrasion of the high speed spinning shaft 64. When closed, the valve 72 forms a positive seal allowing materials to be moved with high vacuum or pressure. The seal 80 is not a rotating seal, hence, the shaft 64 cannot be turning when the seal 80 is engaged. The seal 80 used in the preferred embodiment is made of soft latex rubber which can be expanded with little effort. This allows the operator to expand the seal 80 by compressing it directly, rather than by using a threaded element. By combining the operations of closing the valve 72 and locking the source tubes (not shown) into the valve 72, the operator can never attempt to inject fluids with the valve 72 open resulting in loss of the injected material at the proximal end.

The elements in the sterile field of the system are the guide wire 29, the guide sheath 28, the advancer assembly 16 and the flexible drive shaft 18 from the prime mover 12. These elements can be made of hemo-compatible materials, such as plastic, silicone, and stainless steel. Elements of the system that do not contact the blood, such as the motor drive shaft 18 and drive wheels 35, 50, can be made of steel and aluminum. In all cases the sterile elements of this system 10 have low dimensional tolerance requirements and can be fabricated very inexpensively with low cost being important to disposibility. Cleaning such a system for reuse is very difficult, because of all the areas within it that can entrap fluid with limited access for cleaning. Having disposable elements is an important advantage and it reduces much of the preparation needed to use the system 10.

There are two basic element to the electronic portion of the system 10. The first is the power supply 100, shown schematically in FIG. 8. The power supply 100 which will produce direct current voltages from about 0 through 120 volts. It also has a DC supply to drive the control circuits. The second electronic element is the control circuitry 200, FIG. 9, whichs include current (or load) sensing, triggering, and dynamic braking elements. Both of these elements are housed in controller 30.

Figure 8:
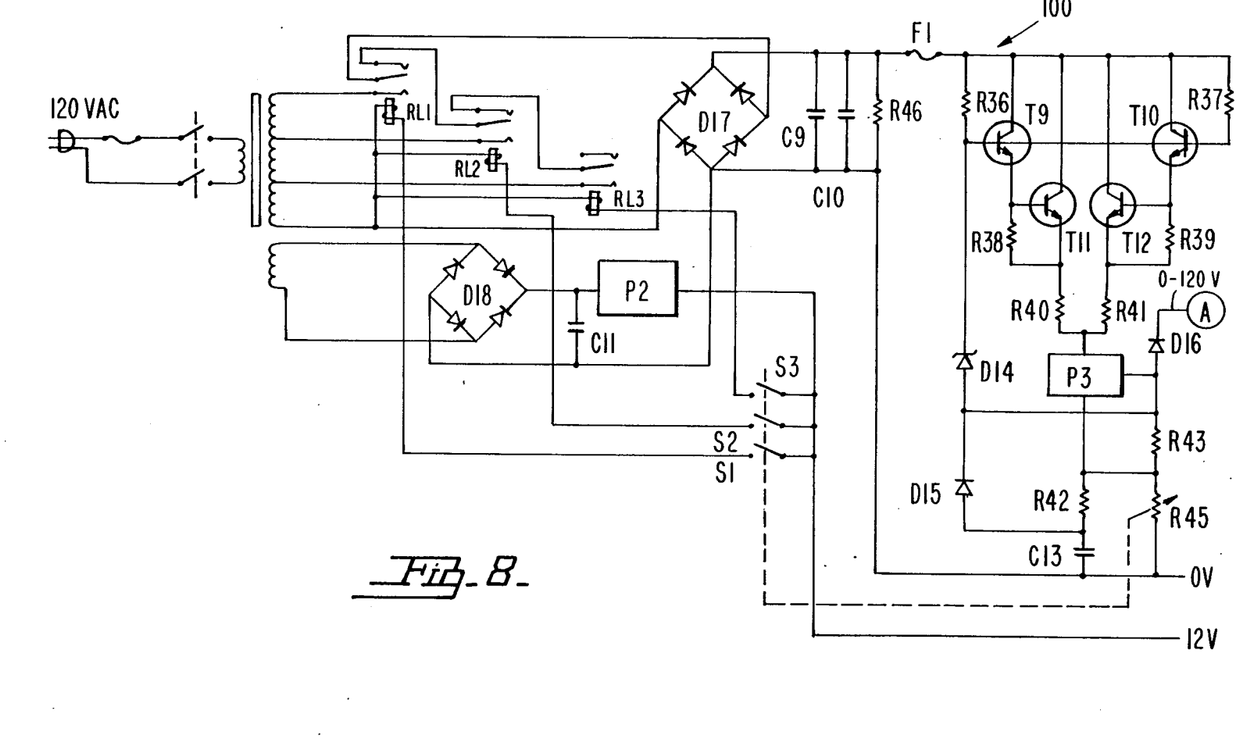
FIGS. 8 and 9 are schematic views of the circuitry used in the power supply of the preferred embodiment of the invention.

The variable output power supply 100 is a high current source capable of up to 2 amps. To allow for this high current with a large voltage variation a stepped supply was needed to limit control element dissipation. This supply uses 3 steps: 0–40 volts, 40–80 volts, and 80–120 volts. In this way, the dissipation in control transistors T11 and T12 will not exceed 80 watts (40 watts each), but the supply 100 is controllable over a 240 watt range. The transistors T9–T12 work as a power gain stage from the control output leg of regulator P3. Regulator P3 operates by establishing a nominal 1.25 V reference voltage between the output and the control leg. This reference voltage is impressed across program resistor R43. Since the voltage is constant a constant current flows through resistor R42. This current drains through variable resistor R45 which can then vary the voltage across it by changing its resistance and, thus, control the output voltage. The variable resistor R45 is placed in the foot pedal 32 along with the voltage switches S1–S3. The switches S1–S3 are synchronized with the variable resistor R45 such that a smooth and continuous transition takes place through the voltage range.

The current sensing portion of the control circuit 200 (See FIG. 9) is comprised of: resistor R5, the biasing network R9–R16 and diodes D4–D9, and operational amplifier P1-1. The voltage across R5, which represents the current through it, is biased down and then amplified to be used in the comparator circuit.

Figure 9:
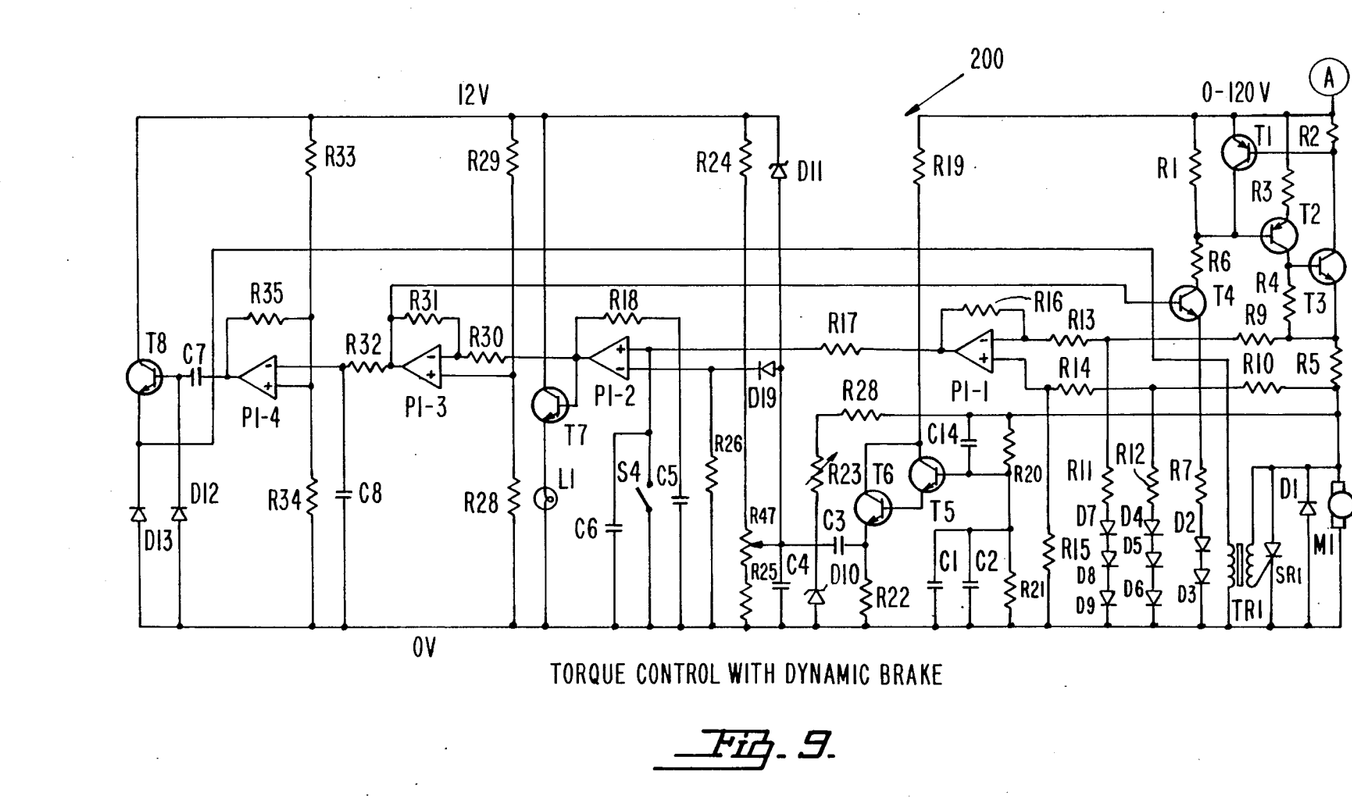

The comparator and latch, P1-2, examines the output from the current sense and bias point set with resistor R47 augmented by the supply voltage and its derivative. A scaled derivative is produced by resistors R19–R22, capacitors C1–C4 and C14, and transistors T5 and T6. The supply voltage augments the trip points divider network R24–R26 through series connected R23 and R28. These elements work together to manipulate the trip point set by R47 such that it is held at equidistance from the motor's load level for motor loads caused by operator induced demand. In this way, the system 200 is sensitive to external loads and not those caused by accelerations or friction of the motor 12 itself.

If the latch, P1-2, is tripped, it is inverted by P1-3 and the signal is used to turn off the transistor switch, T3, removing the power source from the motor 12. The signal is further prepared and delayed by P1-4 to fire the SCR SR1 and short the input lines of the motor 12 to stop it.

As will be obvious to those skilled in the art, the present invention makes use of dynamic torque measurement to test for augering of the burr 20 in atherosclerotic plaque; jamming of the drive catheter 22, caused by breakage or debris, or other malfunctions that would transfer unwanted torque to the vessel itself. The torque sensing equipment is corrected to account for accelerations of the drive system, thereby improving both the safety of the device and its ease of use. The safety is improved, because the torque trip threshold is held apart from the torque due to mechanical energy storage and friction by predetermined amount. In so doing, the angular momentum of the drive system is prevented from interfering with the delivered torque trip threshold. The system 10 is easy to use, because it will not trip out when the operator tries to rapidly accelerate the drive system.

Dynamic braking is used to stop the system 10 in the event of an overload with as little energy transfer to the vessel 26 as possible. The drive catheter 22 is brought to rest by the prime mover 12 rather than by frictional and load losses.

The torque trip point may be set by an easily accessible control. Since the tortuous path required to access lesions is variable, the frictional drag of the drive catheter 22 is equally variable, and, in many cases, it can exceed the maximum torque required by the burr 20 for cutting. This requires that the frictional load be measured with each catheter size and position. This can be done easily by running the system with the burr 20 withdrawn into the distal end of the guide sheath 28 and adjusting the torque trip control down until the rotating elements of the system 10 stop. Then, the torque trip point is advanced appropriately for the situation.

Using an off-axis drive, which is parallel to the drive catheter 22, for coupling rotational energy to the drive catheter 22 by the engagement of two wheels 35, 50 or gears (not shown). This method allows a guide wire 29 to exit coaxially from the drive catheter 22 while having the prime mover 12 located remotely. It also permits the guide wire 29 to be manipulated independently of the drive catheter 22. The off-axis drive also permits easy separation of driven catheters from driving elements, so that catheter changes can be done quickly and easily. The operator can, therefore, assemble the guide wire 29, the drive catheter 22, and the guide sheath 28 combination without having to thread the elements through an axial port of a prime mover.

Using a remote prime mover 12 permits it to be removed from the sterile field. Therefore, the driven portion of the system 10, in the sterile field, can be constructed of inexpensive, disposable components.

The floating clamps on the holders 48, 47 for the guide wire 29 and guide sheath 28, respectively, remove undue friction by eliminating misalignment problems. The holders 47, 48 for the guide sheath 28 and the guide wire 29 are located on the distal and proximal ends of the advancer to allow movement in the plane perpendicular to the drive catheter 22. Movement in the direction of the drive catheter 22 is restricted to allow the carriage 14 to control all advancement of the differential cutting head 20.

Locking the guide wire 29 to the saddle 38 makes it stationary with respect to all movement of the drive catheter 22 and the differential cutting head 20.

The use of a single, round guide rail 36 for the carriage 14 of the advancer 16 allows it to pivot up and down to disengage and engage the guide wire 29 and guide sheath 28 easily without stressing the catheter elements. As the carriage 14 is pivoted down to its operating position, the guide sheath 28 and guide wire 29 slip into their respective holders 47, 48. This aligns the catheter elements along the vertical axis of the holders 47, 48 and speeds assembly.

A snap together approach is used to assemble the catheter engagement coupling 34 into the carriage 14. The catheter engagement coupling 34 is keyed so that it will not rotate once snapped down into the receptacle 44 of the carriage 14. The binding force is sufficient to not allow it to dislodge itself while the system 10 is operating. This method makes catheter changes quick and easy. Also combining the catheter engagement coupling 34 with a rotary union reduces the amount of assembly needed with each catheter change, reduces the size and weight of the drive assembly, and improves its reliability by only requiring one rotating seal.

Injection of fluids down the guide sheath 28 is made possible by the lumen access valve 72. This valve 72, when engaged, seals the catheter sheath lumen at the proximal end such that injections at high pressure are possible. The valve 72 is designed so that the connection of a tube or syringe closes the valve 72. In this way, the operator cannot inject fluids that would otherwise exhaust out the proximal end of the guide sheath 28.

The retractable seal element 80 allows the system 10 to run at any speed with no danger of burning the seal 80. This in turn, allows the use of a very soft seal 80 which can be expanded easily by the operator.

Finally, the use of a continuous, semi-rigid section 78 within a coiled guide wire 29 makes it possible to form a linear seal on the guide wire 29. The placement of the semi-rigid section 78 is variable to accommodate guide wire advancement from the orifice of the differential cutting head 20. Since the semi-rigid section 78 is placed within the guide wire 29 proximal that which enters the body, no loss in performance of the guide wire 29 is experienced.

We claim:

1. An electrodynamic transluminal angioplasty system comprising:
   (a) a prime mover having a drive shaft;
   (b) an advancer assembly comprising a body having a saddle formed therein and a carriage which is adapted to move within said saddle;
   (c) means for connecting a drive wheel in said carriage to said drive shaft of said prime mover;
   (d) catheter engagement coupling means including a driven wheel for connecting a rotatable catheter to said drive wheel, whereby said driven wheel in said catheter engagement coupling means can be driven by said drive wheel in said carriage thereby rotating said catheter.

2. The electrodynamic transluminal angioplasty system of claim 1 wherein said a prime mover is electrically operated.

3. The electrodynamic transluminal angioplasty system of claim 2 further comprising a variable power supply for controlling said prime mover.

4. The electrodynamic transluminal angioplasty system of claim 3 wherein said power supply includes torque limiting means for driving said catheter.

5. The electrodynamic transluminal angioplasty system of claim 1 wherein said drive shaft is a flexible drive shaft.

6. The electrodynamic transluminal angioplasty system of claim 1 wherein said advancer assembly includes a guide rail within said saddle on which said carriage is adapted to slide and on which said carriage can be pivotally raised within said saddle.

7. The electrodynamic transluminal angioplasty system of claim 6 wherein said carriage includes means for releasably receiving and holding said catheter engagement coupling.

8. The electrodynamic transluminal angioplasty system of claim 7 in which said catheter engagement coupling includes a driven wheel which is frictionally engaged by said drive wheel in said carriage when said catheter engagement coupling is pivoted into said carriage.

9. The electrodynamic transluminal angioplasty system of claim 8 wherein said drive wheel is made of aluminum.

10. The electrodynamic transluminal angioplasty system of claim 9 wherein said driven wheel is made of urethane.

11. The electrodynamic transluminal angioplasty system of claim 1 wherein said rotatable catheter includes a hollow, axial lumen through which a guide wire which has been introduced into a vessel of a patient will pass.

12. The electrodynamic transluminal angioplasty system of claim 11 further comprising means for accessing the lumen formed between said guide wire and said hollow drive shaft of said rotatable catheter.

13. The electrodynamic transluminal angioplasty system of claim 1 further comprising a guide sheath which is introduced into the vessel of a patient through which said rotatable catheter is adapted to be introduced.

14. The electrodynamic transluminal angioplasty system of claim 13 further comprising valve means for accessing the lumen formed between said rotatable catheter and said guide sheath.

* * * * *